United States Patent [19]

Wang

[11] Patent Number: 4,895,942

[45] Date of Patent: Jan. 23, 1990

[54] EPOXY COMPOUNDS

[75] Inventor: Pen C. Wang, Houston, Tex.

[73] Assignee: Shell Oil Company, Houston, Tex.

[21] Appl. No.: 245,434

[22] Filed: Sep. 16, 1988

Related U.S. Application Data

[63] Continuation-in-part of Ser. No. 172,054, Mar. 23, 1988, abandoned.

[51] Int. Cl.$^4$ .................. C07D 291/04; C07D 419/04
[52] U.S. Cl. .................. 540/489; 540/490; 540/491; 540/500; 540/501; 540/502; 540/503; 544/2; 544/5; 544/6; 544/65; 544/66; 544/67; 544/71; 544/183; 544/220; 544/230; 548/122; 548/123; 548/124; 548/126; 548/410; 546/16; 546/20
[58] Field of Search ............... 548/409, 122, 123, 124, 548/126, 410; 528/87, 323; 540/490–503; 544/2, 5, 6, 65, 66, 67, 71, 183; 546/16, 20

[56] References Cited
PUBLICATIONS

Blaha et al., Tetrahedron Letters, pp. 3949–3952 (1978), Polycyclic Dialatoms with Inherently Chiral Amide Chromophors.
Bijtas et al., CA 98:52962h (1982), The Mass Spectra of Some Spirodilactams.
The Encyclopedia of Polymer Science and Technology, vol. 6, pp. 209–222 (1968).
Cava et al, J. Am. Chem. Soc., vol. 77, 6022 (1955).
Cava et al, J. Am. Chem. Soc., vol. 79, pp. 1706–1709 (1956).
Pariza et al, Synthetic Communications, vol. 13(3), pp. 243–254 (1983).

Primary Examiner—William R. Dixon, Jr.
Assistant Examiner—Miriam Sohn

[57] ABSTRACT

Novel epoxyalkoxy-containing [4.4] spirodilactams having ring nitrogen atoms in the 1- and the 6- ring positions and having a substituent on each ring nitrogen atom, at least one of which substituents contains an epoxyalkyl moiety. Such epoxy compounds are produced by reaction of a 1-halo-2,3-epoxyalkane and the corresponding hydroxy-containing spirodilactam followed by treatment with strong base.

15 Claims, No Drawings

EPOXY COMPOUNDS

This application is a continuation-in-part of a copending U.S. patent application Ser. No. 172,054, abandoned filed Mar. 23, 1988.

FIELD OF THE INVENTION

This invention relates to a novel class of epoxy-containing monomers of polycyclic structure. More particularly, the invention relates to epoxyalkoxy derivatives of a hydroxyaryl-substituted [4.4] spirodilactam compound having ring nitrogen atoms in the 1- and 6- ring positions and having a substituent on each ring nitrogen atom, at least one of which contains a hydroxyaryl moiety.

BACKGROUND OF THE INVENTION

The class of chemical compounds known as epoxys, epoxides or oxirane compounds has well established utility in the art as the precursor of polymeric resins. Such precursor compounds are characterized by the presence within the molecule of at least one oxacyclopropane group, i.e., the

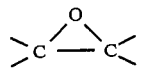

group. The reactive oxygen-containing three-membered ring provides an active site through which reaction takes place, which, in the case of polyfunctional epoxides, is a polymerization reaction. Such polyfunctional epoxides, particularly diepoxides including diglycidyl ethers of dihydroxylic compounds or diglycidyl esters of dibasic acids are well known, as is the reaction of such diepoxy compounds with active hydrogen compounds such as dihydroxylic alcohols or diamines. The resulting polymeric products are thermosetting resins of known commercial utility in adhesives, films and coatings. By way of further illustration, the diglycidyl ether of 2,2-di(4-hydroxyphenyl)propane is an epoxy compound of substantial commercial utility. It is marketed by Shell Chemical Company as EPON® 828 Resin and is also marketed by others. Monofunctional epoxy compounds, although not generally capable of polymerization, are useful as reactive diluents to modify the properties of the polymerized compositions.

The polyfunctional epoxides of cyclic structure are of particular importance in high temperature applications because of the relatively high glass transition temperature their polymeric derivatives typically exhibit. It would be of advantage to provide novel, polycyclic epoxy derivatives which are polymerizable monomers or reactive diluents in the production of thermosetting resins of improved properties.

SUMMARY OF THE INVENTION

The novel epoxy compounds of the invention are epoxyalkoxy derivatives of certain spirodilactams, which spirodilactams having nitrogen atoms in the 1- and 6- ring positions of a [4.4] spiro ring system and have substituents on each spiro ring nitrogen atom, at least one of which substituents contains a hydroxyaryl moiety. Although epoxyalkoxy derivatives of [4.4] spirodilactams of a wide variety of structres are useful as precursors of the epoxy derivatives of the invention, the preferred hydroxyaryl-substituted spirodilactams are represented by the formula

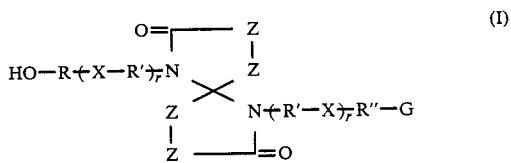

wherein Z independently is $>C(Z')_2$ in which Z' independently is hydrogen, lower alkyl of up to 4 carbon atoms inclusive, preferably methyl or halogen, preferably the lower halogens fluoro or chloro, or Z is such that two adjacent Z moieties taken together form a ring system, Z'', of from 5 to 7 carbon atoms, up to two of which are heteroatoms selected from nitrogen atoms, oxygen atoms and sulfur atoms with the remainder of the Z'' ring atoms being carbon atoms, there being up to 15 carbon atoms inclusive in each Z'', two of which form a bridge connecting a carboxy function carbon, i.e., one of the carbon atoms in the 2- or 7- ring positions of the spiro ring system, with the central or spiro carbon atom, i.e., the carbon atom of the spiro ring system which is common to both spiro rings. In the above formula I, R is aromatic of up to 15 carbon atoms and up to two aromatic rings, inclusive, R' and R'' independently is R or an aliphatic group of up to 10 carbon atoms inclusive. Each of R, R' and R'' independently is hydrocarbyl, i.e., contains only atoms of carbon and hydrogen, or is substituted hydrocarbyl additionally containing atoms other than carbon and hydrogen in the form of inert substituents such as halo, preferably the middle halogens chloro or bromo. The term r is 0 or 1, and G is hydroxy or hydrogen with the proviso that when G is hydroxy then R'' is R. X is a direct valence bond, alkylene of up to 8 carbon atoms inclusive, oxo, thio, sulfonyl, carbonyl, dioxyphenylene, i.e.,

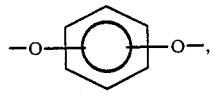

2,2-di(oxyphenyl)propane, i.e.,

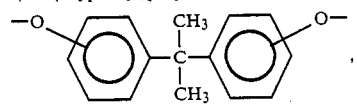

or dioxydiphenylene, i.e.,

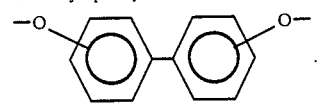

The various modifications of the spirodilactams of the above formula I will be apparent from the formula and the description of the components thereof. However, by way of further illustration, in the embodiment wherein the Z moieties are acyclic, the spirodilactams are exemplified by 1,6-di(4-hydroxyphenyl)-1,6-diazaspiro[4.4]nonane-2,7-dione; 1,6-di(3-hydroxy-4-chlorophenyl)-3,8-dimethyl-1,6-diazaspiro[4.4]nonane-2,7-dione; 1,6-di[4-(4-hydroxyphenyloxy)phenyl]-1,6-diazaspiro[4.4]nonane-2,7-dione; 1,6-di[4-(3-hydroxybenzoyl)phenyl]-1,6-diazaspiro[4.4]nonane-2,7-dione;

1,6-di(4-hydroxyphenyl)-3,3,4,4,8,8,9,9-octamethyl-1,6-diazaspiro[4.4]nonane-2,7-dione; 1,6-di[4-(4'-hydroxybiphenyl)-3,3-dimethyl-1,6-diazaspiro[4.4]nonane-2,7-dione; 1,6-di[2-(4-hydroxyphenyl)propyl]-1,6-diazaspiro[4.4]nonane-2,7-dione; 1-(4-hydroxyphenyl)-6-phenyl-1,6-diazaspiro[4.4]nonane-2,7-dione; 1-[4-(3-hydroxyphenylthio)phenyl]-6-hexyl-1,6-diazaspiro[4.4]nonane-2,7-dione and 1,6-di[4-(4-hydroxyphenylisopropyl)phenyl]-1,6-diazaspiro[4.4]nonane-2,7-dione. In the embodiment wherein adjacent Z moieties on each ring form a cyclic structure fused to the spiro ring system, illustrative spirodilactams include 1,6-di(4-hydroxyphenyl)-3,4,8,9-dibenzo-1,6-diazaspiro[4.4]nonane-2,7-dione; 1,6-di(3-hydroxyphenyl)-3,4,8,9-dipyrido-1,6-diazaspiro[4.4]nonane-2,7-dione; and 1,6-di[4-(4-hydroxyphenyloxy)phenyl]-3,4,8,9-di(cyclopentano)-1,6-diazaspiro[4.4]nonane-2,7-dione. Also suitable are those spirodilactams in which one spiro ring has a fused ring substituent and the other spiro ring is free of fused ring substituents, e.g., 1,6-di(4-hydroxyphenyl)-3,4-benzo-8-methyl-1,6-diazaspiro[4.4]nonane-2,7-dione and 1,6-di[1-(4-hydroxynaphthyl)]-3,4-cyclopentano-1,6-diazaspiro[4.4]nonane-2,7-dione.

In general, the compounds of the above formula I are preferred when R, R' and R'' are hydrocarbon and aromatic and G is hydroxy, particularly such compounds wherein each r is 0. The class of 1,6-di(hydroxyphenyl) spirodilactams is particularly preferred, especially the 1,6-di(4-hydroxyphenyl) spirodilactams. Within the spirodilactam ring portion of the molecule, spirodilactam rings substituted with methyl or hydrogen or fused with benzo rings are generally preferred, particularly the 1,6-diazaspiro[4.4]nonane-2,7-diones spirodilactams.

The hydroxyaryl-substituted spirodilactams of the above formula I are compounds which are described and claimed as compositions of matter in copending U.S. Application Ser. No. 245,618, filed Sept. 16, 1988. The general method of production of the hydroxyaryl-containing spirodilactams, also described and claimed in this copending U.S. application and incorporated herein by reference, is by reaction of at least one primary amino compound and a spirolactam precursor. In terms of the spirodilactam of the above formula I, at least one of the primary amino compounds is represented by the formula

while an optional primary amino compound is represented by the formula

wherein R, R', R'', r, X and G have the previously stated meanings.

The spirodilactam precursor is a 4-oxoheptanedioic acid compound or a spirodilactone of corresponding [4.4] spiro ring structure with lactone oxygen atoms in the 1- and 6- ring positions. In terms of the spirodilactam of the above formula I, the 4-oxoheptanedioic acid compound spirodilactam precursor is represented by the formula

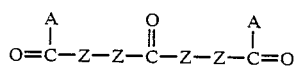

wherein Z has the previously stated meaning and A is hydroxy, lower alkoxy of up to 4 carbon atoms inclusive or halo, preferably middle halo. The spirodilactone spirolactam precursor is represented by the formula

wherein Z has the previously stated meaning.

Many of the acyclic 4-oxoheptanedioic acid compounds are known, but the many of the acyclic esters of formula III are also produced by reaction of formaldehyde and unsaturated carboxylic acid esters by the process disclosed and claimed in copending U.S. patent application Ser. No. 171,999, filed Mar. 23, 1988. Conversion of the esters thereby produced to free acids or acid halides is by conventional methods, as is the interconversion of the acids, esters or acid halides of formula III in general. The production of 4-oxoheptanedioic acid compounds which contain cyclic moieties is by the prcess of Cava et al, J. Am. Chem. Soc., 77 6022 (1955). The production of spirodilactones which are free of additional fused rings is by the process of Pariza et al, Synthetic Communications, Vol. 13 (3), pp. 243–254 (1983). Production of spirodilactones having additional rings fused to the spiro ring system is by the general process of Cava et al, J. Am. Chem. Soc., Vol. 79, pp. 1706–1709 (1957).

The preferred method of producing the hydroxyaryl-containing spirodilactam employed as a precursor of the epoxy compounds of the invention will vary depending upon the nature of the spirodilactam desired. In the case where the substituents on the spiro ring nitrogen atoms are the same, a hydroxyaryl-containing primary amino compound of the formula IIa and the spirolactam precursor are preferably contacted in a molar ratio of amino compound to spirolactam precursor of about 2:1, although in practice, molar ratios as high as 8:1 or as low as about 1.5:1 are satisfactory. When the desired spirodilactam has spiro ring nitrogen substituents which are different, a hydroxyaryl-containing primary amino compound of formula IIa, employed in a limited molar quantity, is reacted with the spirolactam precursor. Molar ratios of amino compound to spirolactam precursor up to about 1.5:1 but preferably about 1:1 are satisfactory. The initial reaction product is a spirolactam-lactone of the formula

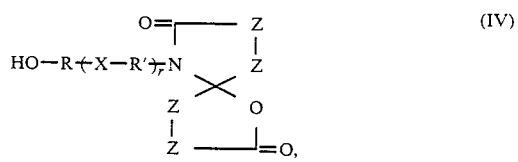

wherein R, R', r, X and Z have the previously stated meanings, which is subsequently reacted with an at least substantially stoichiometric quantity of a primary amino compound of either formula IIa or formula IIb to produce a spirodilactam of formula I with a hydroxyaryl-containing substituent on at least one spiro ring nitrogen atom and a substituent which alternatively will or will not include a hydroxyaryl moiety on the other spiro ring nitrogen atom. Spirodilactams of formula I which incorporate two spiro ring nitrogen atom substituents incorporating hydroxyaryl moieties are preferred. The spirodilactams of differing spiro ring nitrogen atom substituents are also produced by contacting a spirolactam precursor and a mixture of primary amino compounds in which at least one primary amino compound is hydroxyaryl-containing. In general, however, preparation of a spirodilactam of differing spiro ring nitrogen atom substituents is preferably accomplished by a stepwise reaction process involving a spirolactam-spirolactone intermediate.

Reaction of primary amino compounds with a spirolactam precursor or with a spirolactam-lactone intermediate is conducted in a liquid phase solution in an inert reaction diluent such as an N-alkylamide, e.g., N,N-dimethylacetamide, N,N-dimethyformamide or N-methyl-2-pyrrolidone. Reaction takes place under reaction conditions at an elevated temperature, e.g., from about 80° C. to about 250° C., and at a reaction pressure sufficient to maintain the reaction mixture in a liquid phase. Subsequent to reaction, the spirolactam product is recovered, if desired, by conventional methods such as solvent removal, distillation, precipitation or chromatographic separation. However, recovery or purification of a spirolactam product is not required, however. In situations where the initial spirolactam product is a spirolactam-lactone, it is not generally necessary to separate such product before reaction with additional primary amino compound to produce spirodilactam. Particularly in cases where substantially stoichiometric quantities of reactants are employed to produce spirodilactam product, the spirodilactam is suitably employed in situ to produce the epoxyalkyl derivatives of the invention.

The novel epoxyalkyl derivatives are produced by reaction of the spirodilactam of formula I with a 1-halo-2,3-epoxyalkane, preferably of up to 8 carbon atoms inclusive. The halo moieties are preferably middle halo, i.e., chloro or bromo, and illustrative haloepoxy alkane reactants include epichlorohydrin, epibromohydrin, 1-chloro-2,3-epoxyhexane, 1-bromo-2,3-epoxybutane, 1-chloro-2-methyl-2,3-epoxypropane and 1-bromo-2,3-epoxyoctane. The chloroepoxyalkanes are generally preferred over the bromoepoxyalkanes and epihalohydrins are preferred over other haloepoxyalkane reactants. A particularly preferred haloepoxyalkane reactant is epichlorohydrin.

The spirodilactam and the haloepoxyalkane are reacted to produce the novel epoxyalkoxy spirodilactam derivatives of the invention by the conventional methods normally employed for the production of epoxyalkoxy derivatives, particularly glycidyloxy derivatives of hydroxylic compounds such as 2,2-di(4-hydroxyphenyl)propane. The haloepoxyalkane is employed in a molar quantity of at least one mole of haloepoxyalkane per mole of hydroxyl substituent of the spirodilactam. Thus, when the spirodilactam has a single hydroxy-containing substituent, i.e., the term G in formula I is hydrogen, the haloepoxyalkane is employed in a molar quantity of at least one mole of haloepoxyalkane per mole is spirodilactam. When the spirodilactam reactant incorporates two hydroxy-containing substituents, i.e., G in formula I is hydroxy, the molar ratio of haloepoxyalkane reactant to spirodilactam should be at least 2:1. Preferably the haloepoxyalkane is employed in a molar ratio of at least twice the stoichiometric ratio or in an even substantially greater ratio to permit the haloepoxyalkane to serve as a reaction diluent as well as a reactant. Alternatively, other reaction diluents are utilized, e.g., toluene or xylene, so long as the reaction diluent is inert to the reactants and the epoxy-containing product. Reaction is typically conducted at a reaction temperature of from about 80° C. to about 180° C. and a reaction pressure of from about 1 atmosphere to about 10 atmospheres.

Particularly good results are obtained when the reaction of the haloepoxyalkane and the spirodilactam is conducted in the presence of a quaternary phosphonium or ammonium salt as catalyst, particularly those quaternary phosphonium or ammonium salts wherein the substituents on the phosphorus or nitrogen are lower alkyl or phenyl. Alkyltriphenylphosphonium salts, preferably ethyltriphenylphosphonium bromide or iodide, are a preferred class of quaternary phosphonium salts to be used as catalyst. The use of catalyst is not required, but when present the catalyst is employed in quantities of up to about 5% by weight, based on total reactants.

The epoxyalkoxy derivatives of the invention are prepared by contacting the haloepoxyalkane and the spirodilactam under reaction conditions to produce a reaction intermediate which, without isolation, is treated with a strong base, typically aqueous sodium hydroxide or potassium hydroxide, while the water present or formed is removed by distillation under conditions of approximately the normal boiling temperature of the mixture at ambient pressure. Such a two-step process is entirely conventional for the conversion of hydroxyphenyl compounds to corresponding glycidyloxy derivatives by reaction with epichlorohydrin. For example, 2,2-di(4-hydroxyphenyl)propane is converted commercially to the corresponding diglycidyl ether by this technique. Further illustrations and descriptions of this type of process are found in Encyclopedia of Polymer Science and Technology, Vol. 6, pp. 209–222, 1968.

The novel epoxyalkoxy derivatives of the invention as produced by reaction of the haloepoxyalkane and the spirodilactam are epoxyalkoxy derivatives illustratively produced by replacement of the hydrogen of each hydroxyl group of the hydroxy-containing spirodilactam with a 1-(2,3-epoxy)alkyl moiety. In terms of the reactants as described above, the epoxyalkoxyaryl-containing products are represented by the formula

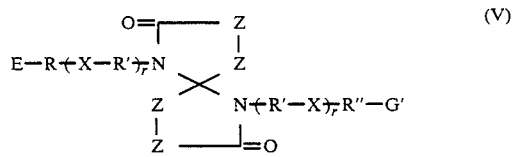
(V)

wherein E is 1-(2,3-epoxy)alkoxy of up to 8 carbon atoms inclusive, G' is hydrogen or E with the proviso that when G' is E then R" is R. R, R', R", r, X and Z have the previously stated meanings.

The identity of specific epoxyalkoxy-containing spirodilactams of the above formula VI will be apparent from description of the reactants and the above formulas. However, the epoxyalkoxy-containing products are exemplified by 1,6-di(4-glycidyloxyphenyl)-1,6-diazaspiro[4.4]nonane-2,7-dione produced by reaction of epichlorohydrin and 1,6-di(4-hydroxyphenyl)-1,6-diazaspiro[4.4]nonane-2,7-dione; 1,6-di[4-(4-glycidyloxyphenyloxy)phenyl]-1,6-diazaspiro[4.4]nonane-2,7-dione produced from epibromohydrin and 1,6-di[4-(4-hydroxyphenyloxy)phenyl]-1,6-diazaspiro[4.4]nonane-2,7-dione; 1-(3-glycidyloxyphenyl)-6-phenyl-1,6-diazaspiro[4.4]nonane-2,7-dione produced from epichlorohydrin and 1-(3-hydroxyphenyl)-6-phenyl-1,6-diazaspiro[4.4]nonane-2,7-dione; 1,6-di[4-(2,3-epoxybutyl)-phenyl]-3,4,8,9-dibenzo-1,6-diazaspiro[4.4]nonane-2,7-dione produced from 1-chloro-2,3-epoxybutane and 1,6-di(4-hydroxyphenyl)-3,4,8,9-dibenzo-1,6-diazaspiro[4.4]nonane-2,7-dione; and 1,6-di(4-glycidylloxyphenyl)-3,4,8,9-dibenzo-1,6-diazaspiro[4.4]nonane-2,7-dione produced from epichlorohydrin and 1,6-di(4-hydroxyphenyl)-3,4,8,9-dibenzo-1,6-diazaspiro[4.4]nonane-2,7-dione.

The novel epoxyalkoxy-substituted spirodilactams of the invention broadly find utility in many of the applications of epoxy derivatives of polyhydroxylic compounds, particularly dihydroxyaromatic compounds. For example, the spirodilactams having two epoxyalkoxy substituents are reacted with polyols or diamine compounds to produce thermosetting resins which are utilized in adhesives, coatings and films by conventional methods. In like manner, the spirodilactams of a single epoxyalkoxy substituent are utilized in such reactions of difunctional compounds as a reactive diluent, i.e., a monomer which undergoes reaction but is not normally involved in polymerization reactions by virtue of having a single reactive site. Use of a reactive diluent serves to modify but not fundamentally alter the properties of a thermosetting resin. A particular application of the epoxyalkoxy-containing spirodilactams of the invention is described and claimed in copending U.S. patent application Ser. No. 245,619, filed Sept. 16, 1988 incorporated herein by reference, where the di-epoxyalkoxy-substituted spirodilactams are reacted with 2,2-di(4-hydroxyphenyl)propane to produce thermoplastic resins of high glass transition temperatures.

The invention is further illustrated by the following Illustrative Embodiments which should not be construed as limiting.

ILLUSTRATIVE EMBODIMENT I

A mixture of 10.14 g (0.03 mole) of 1,6-di(4-hydroxyphenyl)-1,6-diazaspiro[4.4]nonane-2,7-dione, 0.05 g of ethyltriphenylphosphonium bromide and 150 ml of epichlorohydrin is placed in a 500 ml round-bottomed flask equipped with a mechanical stirrer and a condenser. The mixture was stirred while warmed to 120° C. and maintained at 110°–120° C. for 4 hours. The reaction mixture was then cooled to 80°–90° C. while stirring continued and 5.0 g of 50% by weight aqueous sodium hydroxide was added dropwise as the water present or formed was removed by distillation. After addition of the sodium hydroxide, unreacted epichlorohydrin was removed by distillation under reduced pressure and methanol was added to precipitate the product. The precipitated product was washed several times with methanol and then dried in a vacuum over for 24 hours. The product had a melting point of 170° C. and the nuclear magnetic spectra were consistent with the structure 1,6-di(4-glycidyloxyphenyl)-1,6-diazaspiro[4.4]nonane-2,7-dione. The isolated yield was greater than 95%.

ILLUSTRATIVE EMBODIMENT II

A mixture of 10.14 g (0.03 mols) of 1,6-di(3-hydroxyphenyl)-1,6-diazaspiro[4.4]-nonane-2,7-dione, 0.05 g of ethyltriphenylphosphonium bromide and 150 ml of epichlorohydrin was placed in a 500 ml round-bottomed flask equipped with a mechanical stirrer and a condenser. The mixture was stirred while warmed to 120° C. and maintained at 110°–120° C. for 4 hours. The mixture was then cooled to 80°–90° C. while stirring continued and 5.0 g of 50% aqueous sodium hydroxide was added dropwise as the water present or formed was removed by distillation. After addition of the sodium hydroxide, unreacted epichlorohydrin was removed by distillation under reduced pressure and methanol was added to precipitate the product. The precipitated product was washed several times with methanol and then dried in a vacuum oven for 24 hours. The product had a melting point of 126° C. and the nuclear magnetic resonance spectra were consistent with the structure 1,6-di(3-glycidyloxyphenyl)-1,6-diazaspiro[4.4]nonane-2,7-dione.

ILLUSTRATIVE EMBODIMENT III

By the procedure of Illustrative Embodiment II, the compounds 1,6-di(4-glycidyloxyphenyl)-3,4,8,9-dibenzo-1,6-diazaspiro[4.4]nonane-2,7-dione and 1,6-di[4-(4-glycidyloxyphenylisopropyl)phenyl]-1,6-diazaspiro[4.4]nonane-2,7-dione are produced by reaction of epichlorohydrin and the corresponding 4-hydroxy-containing spirodilactam.

What is claimed is:

1. The epoxyalkoxy-containing spirodilactam represented by the formula

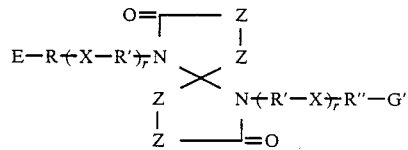

wherein Z independently is =C(Z')$_2$ in which Z' independently is hydrogen, lower alkyl or halogen, or Z is such that two adjacent Z moieties form a ring system Z'' of from 5 to 7 ring atoms up to two of which are nitrogen, oxygen or sulfur with the remainder of the Z'' ring atoms being carbon atoms, there being up to 15 carbon atoms inclusive in Z'', two of which connect a carbonyl carbon atom with the spiro carbon atom, R is aromatic of up to 15 carbon atoms and up to two aromatic rings inclusive, R' or R'' independently are R or aliphatic of up to 10 carbon atoms inclusive, r independently is 0 or 1, X is a direct valence bond, alkylene of up to 8 carbon atoms inclusive, oxo, thio, sulfonyl, carbonyl, dioxyphenylene, 2,2-di(oxyphenyl)propane or dioxydiphenylene, E is 1-(2,3-epoxy)alkoxy of up to 8 carbon atoms inclusive and G' is hydrogen or E with the proviso that when G' is E then R'' is R.

2. The epoxyalkoxy-containing spirodilactam of claim 1 represented by the formula

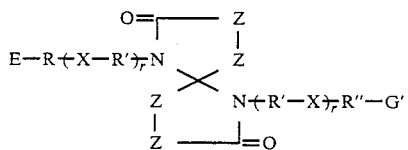

wherein Z independently is <=C(Z')$_2$ in which Z' independently is hydrogen or lower alkyl or Z is such that two adjacent Z moieties form a ring system Z'' of from 5 to 7 ring atoms up to two of which are nitrogen, oxygen or sulfur with the remainder of the Z" ring atoms being carbon atoms, there being up to 15 carbon atoms inclusive in Z", two of which connect a carbonyl carbon atom with the spiro carbon atom, R is aromatic of up to 15 carbon atoms and up to two aromatic rings inclusive, R' or R" independently are R or aliphatic of up to 10 carbon atoms inclusive, r independently is 0 or 1, X is a direct valence bond, alkylene of up to 8 carbon atoms inclusive, oxo, thio, sulfonyl, carbonyl, dioxyphenylene, 2,2-di(oxyphenyl)propane or dioxydiphenylene, E is 1-(2,3-epoxy)alkoxy of up to 8 carbon atoms inclusive and G' is hydrogen or E with the proviso that when G' is E then R" is R.

3. The epoxyalkoxy-containing spirodilactam of claim 2 wherein each of E and G' are glycidyloxy.

4. The glycidyloxy-containing spirodilactam of claim 3 wherein each r is 0.

5. The glycidyloxy-containing spirodilactam of claim 4 wherein Z independently is $>C(Z')_2$ in which Z' independently is hydrogen, methyl, fluorine or chlorine.

6. The glycidyloxy-containing spirodilactam of claim 5 of the structure 1,6-di(glycidyloxyphenyl)-1,6-diazaspiro[4.4]nonane-2,7-dione.

7. The glycidyloxy-containing spirodilactam of claim 6 of the structure 1,6-di(4-glycidyloxyphenyl)-1,6-diazaspiro[4.4]nonane-2,7-dione.

8. The glycidyloxy-containing spirodilactam of claim 6 of the structure 1,6-di(3-glycidyloxyphenyl)-1,6-diazaspiro[4.4]nonane-2,7-dione.

9. The glycidyloxy-containing spirodilactam of claim 4 of the structure 1,6-di[4-(4-glycidyloxyphenylisopropyl)phenyl]-1,6-diazaspiro[4.4]nonane-2,7-dione.

10. The glycidyloxy-containing spirodilactam of claim 4 wherein each Z, together with the adjacent Z moiety, forms a ring system Z".

11. The glycidyloxy-containing spirodilactam of claim 10 wherein each Z" is cyclopentano.

12. The glycidyloxy-containing spirodilactam of claim 10 wherein each Z" is benzo.

13. The glycidyloxy-containing spirodilactam of claim 12 of the structure 1,6-di(glycidyloxyphenyl)-3,4,8,9-dibenzo-1,6-diazaspiro[4.4]nonane-2,7-dione.

14. The glycidyloxy-containing spirodilactam of claim 13 of the structure 1,6-di(4-glycidyloxyphenyl)-3,4,8,9-dibenzo-1,6-diazaspiro[4.4]nonane-2,7-dione.

15. The glycidyloxy-containing spirodilactam of claim 13 of the structure 1,6-di(3-glycidyloxyphenyl)-3,4,8,9-dibenzo-1,6-diazaspiro[4.4]nonane-2,7-dione.

* * * * *